(12) United States Patent
Sato et al.

(10) Patent No.: US 7,871,984 B2
(45) Date of Patent: Jan. 18, 2011

(54) METHYLATED CPG POLYNUCLEOTIDE

(75) Inventors: Yukio Sato, 16-31, Kamihamacho, Fukushima-shi, Fukushima 960-8134 (JP); Hiroko Kobayashi, Fukushima (JP)

(73) Assignees: Yukio Sato, Fukushima (JP); Taisho Pharmaceutical Co., Ltd., Tokyo (JP)

( * ) Notice: Subject to any disclaimer, the term of this patent is extended or adjusted under 35 U.S.C. 154(b) by 147 days.

(21) Appl. No.: 10/553,948

(22) PCT Filed: Apr. 23, 2004

(86) PCT No.: PCT/JP2004/005935

§ 371 (c)(1), (2), (4) Date: Dec. 4, 2006

(87) PCT Pub. No.: WO2004/094448

PCT Pub. Date: Nov. 4, 2004

(65) Prior Publication Data

US 2008/0200407 A1 Aug. 21, 2008

(30) Foreign Application Priority Data

Apr. 23, 2003 (JP) .............................. 2003-118999

(51) Int. Cl.
*A01N 43/04* (2006.01)
(52) U.S. Cl. ....................................................... 514/44
(58) Field of Classification Search ...................... None
See application file for complete search history.

(56) References Cited

U.S. PATENT DOCUMENTS

| 6,579,860 | B1 | 6/2003 | Koike et al. | |
|---|---|---|---|---|
| 6,653,292 | B1 * | 11/2003 | Krieg et al. | 514/44 |
| 6,949,520 | B1 | 9/2005 | Hartmann et al. | |
| 2004/0097465 | A1 | 5/2004 | Asari et al. | |
| 2004/0248834 | A1 | 12/2004 | Klinman et al. | |
| 2005/0169888 | A1 | 8/2005 | Hartmann et al. | |
| 2006/0074039 | A1 | 4/2006 | Klinman et al. | |

FOREIGN PATENT DOCUMENTS

| JP | 2002-521489 | | 7/2002 |
|---|---|---|---|
| JP | 2003-510290 | | 3/2003 |
| WO | WO 98/01880 | * | 5/1998 |
| WO | WO/98/18810 | * | 5/1998 |
| WO | 00/06588 | | 2/2000 |
| WO | 00/38693 | | 6/2000 |
| WO | 01/22990 | | 4/2001 |
| WO | WO/01/48245 | * | 7/2001 |
| WO | 01/75092 | | 10/2001 |
| WO | 02/074318 | | 9/2002 |
| WO | 03/027313 | | 4/2003 |

OTHER PUBLICATIONS

Infante-Duarte et al., Th1/Th2 balance in infection. Springer Seminars in Immunopathology, 1999, 21: 317-338.*
Katoaka et al (Jpn. J. Cancer Res. 1992 vol. 83 pp. 244-247.*
Chu et al 1997 CpG Oligodeoxynucleotides Act as Adjuvants that Switch on T Helper 1 (TH1) Immuntiy pp. 1623-1630.*
Weiner et al 1997 Proc. Natl. Acad. Sci. USA vol. 94 pp. 10833-10837.*
Sugiyama et al 1996 Nucleic Acids Research vol. 24 No. 7 pp. 1272-1278.*
Zharkov et al 2000 vol. 275 No. 37 pp. 28607-28617.*
Gaffney et al 1984 Biochemistry vol. 23 pp. 5686-5691.*
Churchwell et al 2006 Journal of Chromatography pp. 60-66.*
Kalnik et al., "$O^6$-Ethylguanine Carcinogenic Lesions in DNA: An NMR Study of $O^6$etG•C Pairing in Dodecanucleotide Duplexes", Biochemistry, vol. 28 (1989), pp. 6182-6192.
Kawai et al., "Intrastrand 2'β Hydrogen Abstraction of 5'-Adjacent Deoxyguanosine by Deoxyuridin-5-yl in Z-form DNA", Tetrahedron Letters, vol. 40 (1999), pp. 2589-2592.
Lee et al., "DNA Microstructural Requirements for Neocarzinostatin Chromophore-induced Direct Strand Cleavage", Nucleic Acids Research, vol. 17, No. 14 (1989), pp. 5809-5825.
Zhao et al., "Site of Chemical Modifications in CpG Containing Phosphorothioate Oligodeoxynucleotide Modulates Its Immunostimulatory Activity", Bioorganic & Medicinal Chemistry Letters, vol. 9 (1999), pp. 3453-3458.
Sato et al., "Immunostimulatory DNA Sequences Necessary for Effective Intradermal Gene Immunization", Science, vol. 273 (1996), pp. 352-354.
Krieg et al. "CpG Motifs in Bacterial DNA Trigger Direct B-cell Activation", Nature, vol. 374 (1995), pp. 546-549.
Miyata et al., "Unmethylated Oligo-DNA Containing CpG Motifs Aggravates Collagen-Induced Athritis in Mice", Athritis & Rheumatism, vol. 43, No. 11 (2000), pp. 2578-2582.
Leadbetter et al., "Chromatin-IgG Complexes Activate B-cells by Dual Engagement of IgM and Toll-like Receptors", Nature, vol. 416 (2002), pp. 603-607.
Office Action issued in counterpart Japanese application, dated Sep. 14, 2010.

* cited by examiner

*Primary Examiner*—N. M Minnifield
*Assistant Examiner*—Nina A Archie
(74) *Attorney, Agent, or Firm*—Greenblum & Bernstein, P.L.C.

(57) ABSTRACT

It is an object of the present invention to provide a polynucleotide, which can effectively suppress the immunoreactivity caused by DNA having a CpG motif and which can be used for preventing and/or treating immune-mediated diseases such as arthritis. The present invention provides a polynucleotide comprising a CpG motif wherein guanine is methylated, and a pharmaceutical composition comprising the above-mentioned polynucleotide.

4 Claims, 2 Drawing Sheets

METHYLATED CPG POLYNUCLEOTIDE

TECHNICAL FIELD

The present invention relates to a polynucleotide having action to suppress the immunoreactivity of a CpG motif. More specifically, the present invention relates to a polynucleotide, which has action to suppress the immunoreactivity of a CpG motif and can be used for preventing and/or treating immune-mediated diseases such as arthritis, and a pharmaceutical composition comprising the above-mentioned polynucleotide as an active ingredient.

BACKGROUND ART

Components derived from microorganisms have immunoreactivity. In particular, it has been known that DNA contained in a large amount in the bacterial components of *Mycobacterium tuberculosis* has strong action to activate natural immunity and functions as an adjuvant for inducing a T helper type 1 immune reaction to an antigen (Science 273; 352-354, 1996). It has also been known that the action of this DNA to activate immunity is derived from DNA having a CpG motif (CpG DNA) and that such immunoreactivity is lost by alternation of the sequence or methylation of cytosine (Nature 374; 546-549, 1995).

On the other hand, there has been a report suggesting the possibility that such DNA derived from microorganisms is associated with the pathologic conditions of autoimmune diseases including articular rheumatism as a typical example (Arthritis Rheum 43; 2578-2582, 2000, Nature 416; 603-607, 2002).

JP Patent Publication (Kohyo) No. 2002-521489 A describes that the S-stereoisomer of DNA containing CpG is able to stimulate immunity, and that such CpG-containing DNA can be used as a vaccine adjuvant, or as a factor for activating immunity to prevent or treat virus diseases, parasitic diseases, or fungus diseases, or it can also be used in immunotherapy for cancers, allergic diseases or asthma. Moreover, JP Patent Publication (Kohyo) No. 2002-521489 A also describes that the R-stereoisomer of CpG-containing DNA is able to suppress the aforementioned effect of the S-stereoisomer to stimulate immunity.

DISCLOSURE OF THE INVENTION

It is an object of the present invention to provide a polynucleotide, which can effectively suppress the immunoreactivity caused by DNA having a CpG motif and which can be used for preventing and/or treating immune-mediated diseases such as arthritis, and a pharmaceutical composition comprising the above-mentioned polynucleotide as an active ingredient.

As a result of intensive studies directed towards achieving the aforementioned object, the present inventors have found that the generation of interleukin 6 (IL-6) and interleukin 12 (IL-12) can effectively be suppressed by administration of DNA containing a CpG motif wherein guanine is methylated, to a mouse bone marrow-derived macrophage. In addition, the present inventors have also found that arthritis can effectively be suppressed, when DNA containing a CpG motif wherein guanine is methylated, is administered to an arthritis model mouse. The present invention has been completed based on these findings.

Thus, the present invention provides a polynucleotide comprising a CpG motif wherein guanine is methylated.

Preferably, the length of the polynucleotide of the present invention consists of 8 to 100 nucleotides.

Preferably, the polynucleotide of the present invention comprises the nucleotide sequence shown in any one of SEQ ID NOS: 1 to 4, and more preferably consists of the nucleotide sequence shown in any one of SEQ ID NOS: 1 to 4.

In another aspect, the present invention provides a pharmaceutical composition which comprises the aforementioned polynucleotide of the present invention as an active ingredient.

Preferably, the pharmaceutical composition of the present invention is a pharmaceutical composition for preventing and/or treating immune-mediated diseases. More preferably, the pharmaceutical composition of the present invention can be used as an immunosuppressive agent or an agent for treating arthritis.

In another aspect, the present invention provides an agent for suppressing generation of interleukin, which comprises the aforementioned polynucleotide of the present invention as an active ingredient.

In another aspect, the present invention provides a method for preventing and/or treating immune-mediated diseases, a method for suppressing immunity, a method for treating arthritis, and a method for suppressing generation of interleukin, which comprise a step of administering an effective amount of polynucleotide comprising a CpG motif wherein guanine is methylated, to mammals including humans.

In another aspect, the present invention provides the use of a polynucleotide comprising a CpG motif wherein guanine is methylated, for the production of a pharmaceutical composition for preventing and/or treating immune-mediated diseases, an immunosuppressive agent, an agent for treating arthritis, or an agent for suppressing generation of interleukin.

BEST MODE FOR CARRYING OUT THE INVENTION

Figure 1:
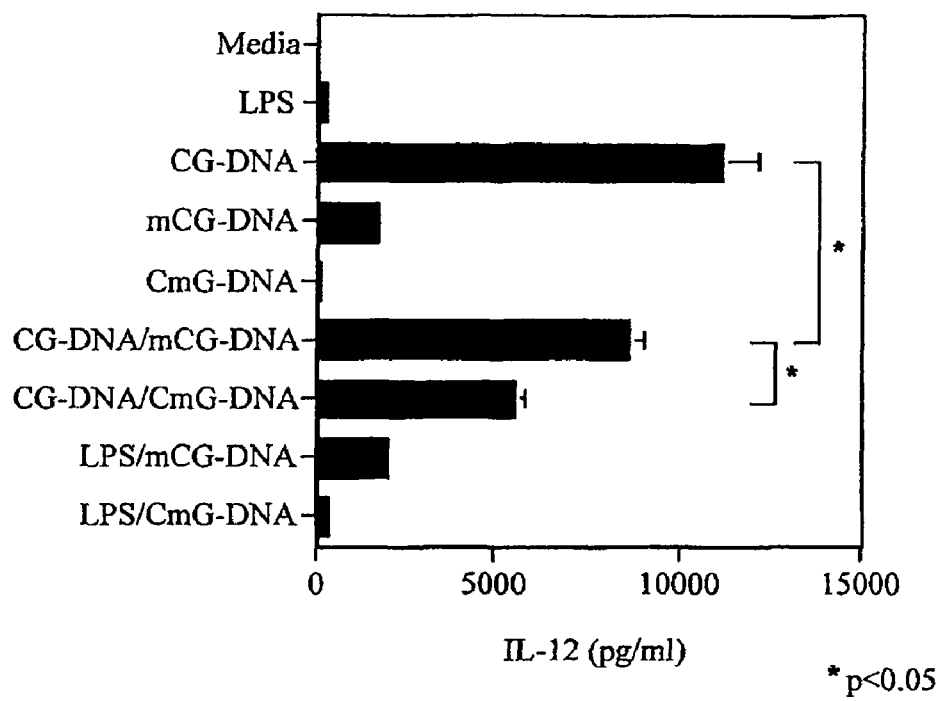
FIG. 1 shows the results regarding suppression of the induction of IL-12 and IL-6 from macrophage by mCG-DNA or CmG-DNA.
Figure 1:
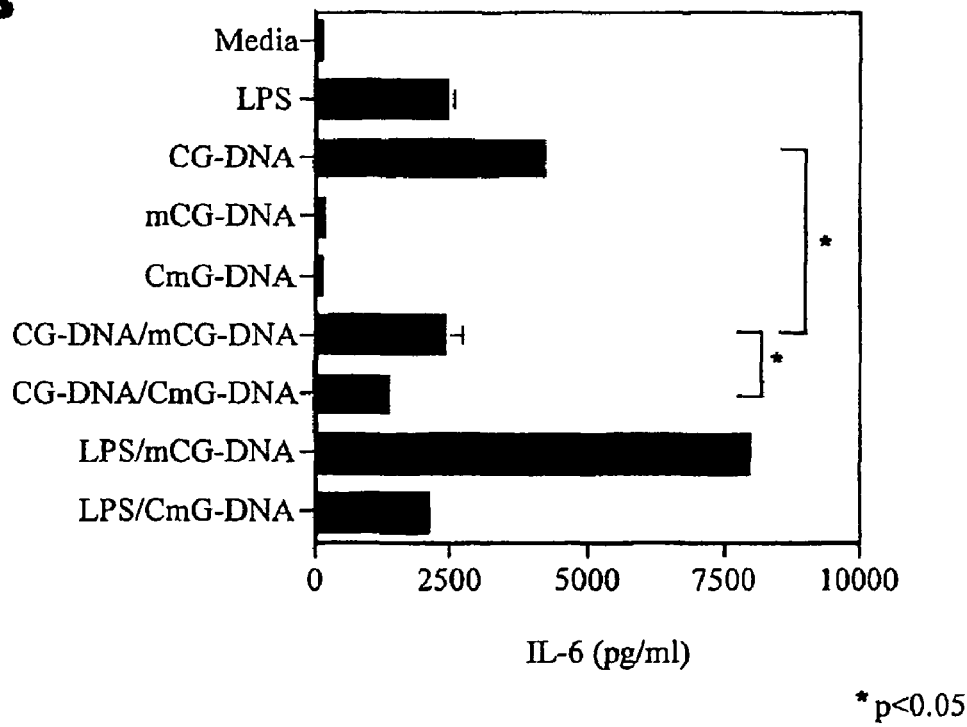
Figure 2:
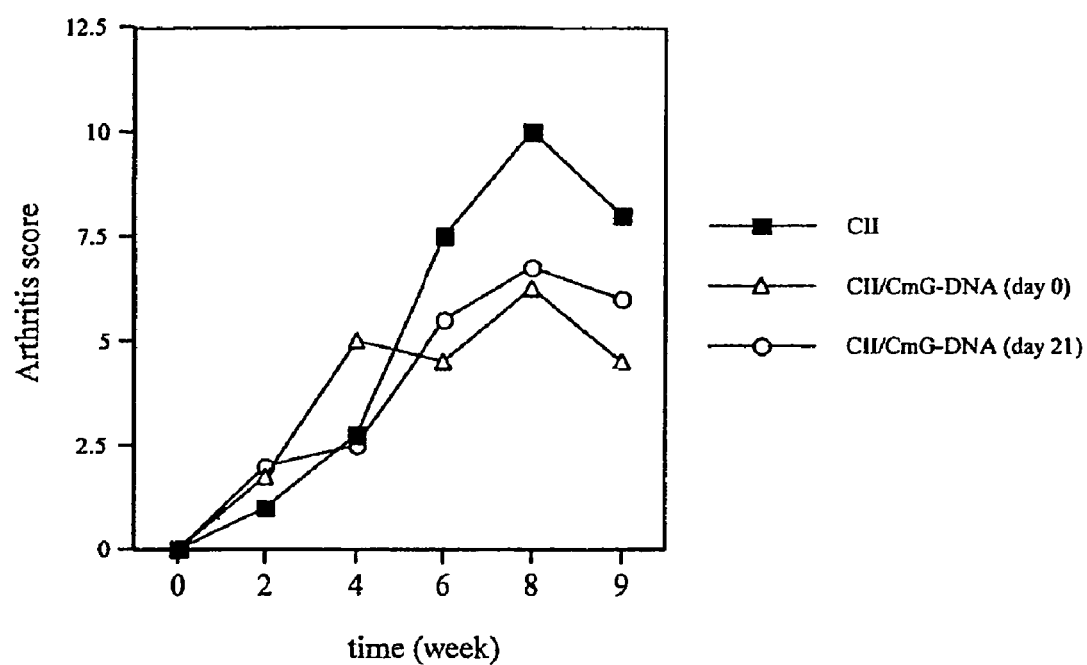
FIG. 2 shows the effects of CmG-DNA on type II collagen arthritis model mice. Day 0 indicates that CmG-DNA was administered for the first immunization. Day 21 indicates that CmG-DNA was administered for the booster conducted 3 weeks after the first immunization.

The embodiments of the present invention will be described in detail below.

(Polynucleotide)

The polynucleotide of the present invention is characterized in that it comprises a CpG motif wherein guanine is methylated. The polynucleotide of the present invention may be either a polyribonucleotide or a polydeoxyribonucleotide. The CpG motif is used in the present specification to mean a nucleotide sequence comprising cytosine (C) and guanine (G). The polynucleotide of the present invention may be either a single-stranded or a double-stranded. In addition, it may be either linear or cyclic. The length of the polynucleotide of the present invention is not particularly limited, as long as the effects of the present invention to suppress immunoreactivity can be achieved. From the viewpoint of easy incorporation thereof into cells, it preferably consists of 8 to 100 nucleotides, and more preferably consists of 8 to 30 nucleotides.

C in the CpG motif may be either a ribonucleotide or deoxyribonucleotide, which has an unmethylated or methylated cytosine as a base. From the results of a test regarding suppression of the generation of interleukin-6 and interleukin-12, it was confirmed that the polynucleotide of the present invention comprising a CpG motif having a methylated cytosine exhibits the same level of action to suppress the generation of IL-6 and IL-12 as that of the polynucleotide of the present invention comprising a CpG motif having an unmethylated cytosine.

Methylated G in the CpG motif means a ribonucleotide or deoxyribonucleotide, which has a methylated guanine as a base. Examples of a site to be methylated may include positions 2, 6, and 7 of guanine. A preferred example may be methylation of a ketone group at position 6.

Nucleotides other than such a CpG motif may be riboses or deoxyriboses which are substituted with pyrimidine or purine. Specific examples thereof may include riboses or deoxyriboses, which have guanine, adenine, cytosine, thymine, or uracil, as a base.

The polynucleotide of the present invention can also be used as a polynucleotide derivative by substituting a part of nucleotides with nucleotide derivatives, as long as it does not impair the action of a methylated CpG motif to suppress immunity. Specific examples of such a polynucleotide derivative may include: a polynucleotide derivative wherein a phosphate diester bond in the polynucleotide is converted into a phosphorothioate bond; a polynucleotide derivative wherein a phosphate diester bond in the polynucleotide is converted into an N3'-P5' phosphoamidate bond; a polynucleotide derivative wherein a ribose and a phosphate diester bond in the polynucleotide are converted into a peptide nucleic acid bond; a polynucleotide derivative wherein an uracil in the polynucleotide is substituted with a C-5 propynyl uracil; a polynucleotide derivative wherein an uracil in the polynucleotide is substituted with a C-5 thiazole uracil; a polynucleotide derivative wherein a cytosine in the polynucleotide is substituted with a C-5 propynyl cytosine; a polynucleotide derivative wherein a cytosine in the polynucleotide is substituted with a phenoxazine-modified cytosine; a polynucleotide derivative wherein a ribose in the polynucleotide is substituted with a 2'-O-propyl ribose; and a polynucleotide derivative wherein a ribose in the polynucleotide is substituted with a 2'-methoxyethoxy ribose. However, examples are not limited thereto.

The basic sequence of a nucleic acid having the polynucleotide of the present invention includes 5'-purine-purine-CmG-pyrimidine-pyrimidine. Specific examples of such a sequence may include:

```
5'-TCCATGACmGTTCCTGATGCT-3';    (SEQ ID NO: 1)

5'-TCCATGTCmGTCCCTGATGCT-3';    (SEQ ID NO: 2)

5'-GCTAGACmGTTAGCGT-3';         (SEQ ID NO: 3)

and

5'-TCCATAACmGTTCCTGATGCT-3'.    (SEQ ID NO: 4)
```

The polynucleotide of the present invention can be produced by methods known to persons skilled in the art, such as the gene recombination technique, the nucleic acid synthesis, or the site-directed mutagenesis. For example, a polynucleotide or a polynucleotide derivative may directly be synthesized using a DNA synthesizer, in accordance with the nucleic acid synthesis that is generally used in genetic engineering. A portion of such a polynucleotide may be synthesized, and it may be then amplified by the PCR method or using a cloning vector or the like. Moreover, as mentioned above, in order to obtain a polynucleotide derivative that is stable in cells, a base, a sugar, and a phosphoric acid portion may chemically be modified. Examples of the aforementioned polynucleotide synthesis method may include the phosphate triester method, the phosphoramidite method, and the H-phosphonate method.

A polynucleotide wherein guanosine is methylated at position 6 may be produced using the following compound as a starting material, for example:

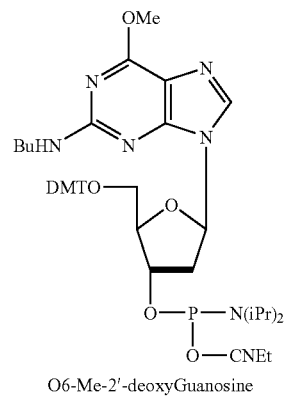

O6-Me-2'-deoxyGuanosine (Pharmaceutical Composition for Preventing or Treating Immune-Mediated Diseases)

As described later in test examples of the present specification, it has been confirmed that the polynucleotide of the present invention comprising a CpG motif wherein guanine is methylated can suppress the generation of interleukin when a mouse bone marrow-derived macrophage is stimulated with CpG DNA or the like, and that it can also suppresses arthritis in type II collagen arthritis model mice. That is to say, the present invention provides a pharmaceutical composition comprising, as an active ingredient, a polynucleotide having a CpG motif wherein guanine is methylated. The pharmaceutical composition of the present invention has action to suppress immunity, and thus, it can be used for preventing and/or treating immune-mediated diseases. The pharmaceutical composition of the present invention can be used for preventing and/or treating autoimmune diseases such as articular rheumatism, systemic lupus erythematosus, diabetes, multiple sclerosis, Hashimoto's disease, hemolytic anemia, myasthenia gravis, scleroderma, ulcerative colitis, or idiopathic thrombocytopenic purpura; allergic diseases such as chronic bronchial asthma, atopic dermatitis, contact dermatitis, pollinosis, or allergic rhinitis; graft-versus-host disease; immunological rejection occurring during organ transplantation; acute infectious disease whose etiologic agent is considered to be activation of the immune system caused by enterotoxin; or arteriosclerosis. From another viewpoint, the polynucleotide of the present invention can also be used as an agent for suppressing generation of interleukin.

When the polynucleotide of the present invention is used in the form of a pharmaceutical composition, the aforementioned polynucleotide is used as an active ingredient, and a pharmaceutically acceptable carrier, diluent, stabilizer, excipient, or the like are further used, so as to prepare a pharmaceutical composition.

When the pharmaceutical composition of the present invention is administered to a patient, the administration route is not particularly limited. Either an oral administration or a parenteral administration may be applied. The pharmaceutical composition can be administered by methods known to persons skilled in the art. Examples of a preferred administration route may include an intra-arterial injection, an intravenous injection, and a hypodermic injection.

In the case of an oral administration, the pharmaceutical composition of the present invention can be used in a dosage form suitable for oral administration, such as a tablet, a hard or soft gelatin capsule, a solution, an emulsion, or a suspension. In the case of a parenteral administration, the pharmaceutical composition of the present invention may be administered into the rectum in the form of a suppository, for example. Otherwise, it may also be administered in the form of a solution used for injection via an intra-arterial injection, an intravenous injection, or a hypodermic injection.

In order to prepare the pharmaceutical composition of the present invention, the polynucleotide of the present invention can be mixed with a pharmaceutically acceptable excipient, for example. Specific examples of such an excipient used for tablets or gelatin capsules may include lactose, corn starch or a derivative thereof, and stearic acid or a salt thereof. Examples of an excipient suitable for production of a solution may include water, polyol, sucrose, invert sugar, and glucose. Examples of an excipient suitable for production of an injection solution may include water, alcohol, polyol, glycerol, and vegetable oil. Examples of an excipient suitable for production of a suppository may include vegetable oil, hydrogenated oil, wax, fat, and semi-liquid polyol. In addition, to the pharmaceutical composition of the present invention, an antiseptic, a solvent, a stabilizer, a wetting agent, an emulsifier, a sweetener, a dye, a flavor, a salt used for changing the osmotic pressure, a buffer, a coating agent, an antioxidant, and further, a compound having another type of therapeutic activity, may be added, as desired.

The dosage of the polynucleotide of the present invention differs depending on the body weight of a patient, the age thereof, an administration method, etc. It is possible for persons skilled in the art to appropriately select a suitable dosage. The dosage of the polynucleotide as an active ingredient is generally between approximately 0.1 and 100 mg/kg per once.

The present invention will be more specifically described in the following examples. However, the examples are not intended to limit the scope of the present invention.

EXAMPLES

Test Example 1

(Method)

Preparation of BMDM and the measurement of cytokine were carried out in accordance with the method of Martin-Orozco et al. (Int Immunol 1999, 11: 1111-1118).

Bone marrow derived macrophage (BMDM) prepared from the bone marrow cells of BALB/c mice was adjusted to a concentration of $2 \times 10^5$ cells/ml. It was then cultured together with each of CG-DNA (1 μg/ml), mCG-DNA (10 μg/ml), CmG-DNA (10 μg/ml), and LPS (100 ng/ml, *E. coli* 0111: B4 (Sigma L-4391)), on a DMEM medium (Sigma) for 24 hours. 24 hours later, the culture supernatant was recovered, and the concentration of IL-12 and that of IL-6 in the supernatant were measured by ELISA (FIG. 1). A significant difference test was carried out using StatView.

It is to be noted that synthetic DNAs (all of which were 5'-S phosphorylated; 1-micro-HPLC purified products) were synthesized by the β-cyanoethylamidite method, then purified by common methods known to persons skilled in the art, and then used.

```
DNA comprising a CpG motif (CG-DNA):
5'-TCCATGACGTTCCTGATGCT-3';       (SEQ ID NO: 5)

DNA comprising a CpG motif wherein C is methylated
(mCG-DNA):
5'-TCCATGAmCGTTCCTGATGCT-3';      (SEQ ID NO: 6)

DNA comprising a CpG motif wherein G is methylated
(CmG-DNA):
5'-TCCATGACmGTTCCTGATGCT-3'.      (SEQ ID NO: 1)
```

(In the test example, mC represents 5-methyl-2'-deoxycytidine, and mG represents O6-methyl-2'-deoxyguanosine.)

(Results)

Mouse bone marrow-derived macrophage was cultured in vitro together with LPS or CG-DNA, while mCG-DNA or CmG-DNA was added thereto. 24 hours later, the culture supernatant was recovered, and the concentration of IL-12 and that of IL-6 in the supernatant were measured. The induction of IL-12 and IL-6 from the macrophage by CG-DNA was suppressed by mCG-DNA or CmG-DNA. CmG-DNA had a higher effect of suppressing the induction of IL-12 and IL-6 than mCG-DNA did. In addition, it was also shown that CmG-DNA did not suppress the induction of IL-6 by LPS, and that mCG-DNA rather enhanced it.

Test Example 2

(Method)

A test using a mouse type II collagen arthritis model was carried out in accordance with Current protocols in immunology: 15.5.1-15.5.14.

A DBA/1LacJ mouse (8-week-old, female) was immunized with type II collagen (CII) (Koken) and Complete Freund Adjuvant (DIFCO). 3 weeks later, a booster was carried out with type II collagen (CII) and Incomplete Freund Adjuvant, thereby producing a type II collagen arthritis model.

As described below, synthetic DNA was hypodermically administered to the above mouse, and the arthritis score was measured once a week. The arthritis score was measured in accordance with Current protocols in immunology.

TABLE 1

| | Dosage | Administration method |
|---|---|---|
| CII | 200 μg | s.c.; at the hip |
| CFA | Equal volume to CII | s.c.; at the hip |
| IFA | Equal volume to CII | s.c.; at the hip |
| CmG | 50 μg | i.d.; at the base of the tail |

CII: Type II collagen
CFA: Complete Freund adjuvant
IFA: Incomplete Freund adjuvant
CmG: CmG-DNA

TABLE 2

|  | day 0 | day +21 |
|---|---|---|
| CII | CII/CFA | CII/IFA |
| CII/CmG (0) | Cn/CFA + CmG | CII/IFA |
| CII/CmG (21) | CII/CFA | CII/IFA + CmG |

(Results)

When CmG-DNA was administered for the first immunization (day 0) or for the booster conducted 3 weeks after the first immunization (day 21), arthritis was suppressed.

This result suggests that CmG-DNA inhibits toll like receptor (TLR) 9 specifically and more effectively than the known synthetic DNAs, and thus that CmG-DNA is useful for the treatment of autoimmune diseases.

INDUSTRIAL APPLICABILITY

The polynucleotide of the present invention effectively suppresses the generation of IL-6 and IL-12 by CpG DNA. Thus, the present polynucleotide can be used for preventing and/or treating autoimmune diseases such as articular rheumatism, allergic diseases such as allergic rhinitis, multiple myeloma, mesangial proliferative nephritis, etc.

The invention claimed is:

1. A polynucleotide comprising a CpG motif wherein guanine of the CpG motif is methylated and the methylated guanine is 6-O-methyl-2'-deoxyguanosine which comprises the nucleotide sequence shown in any one of SEQ ID NOS: 1 to 4.

2. The polynucleotide comprising a CpG motif wherein guanine of the CpG motif is methylated and the methylated guanine is 6-O-methyl-2'-deoxyguanosine which consists of the nucleotide sequence shown in any one of SEQ ID NOS: 1 to 4.

3. A pharmaceutical composition which comprises the polynucleotide of claim 1 as an active ingredient and at least one pharmaceutically acceptable excipient.

4. A pharmaceutical composition which comprises the polynucleotide of claim 2 as an active ingredient and at least one pharmaceutically acceptable excipient.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (9)
<223> OTHER INFORMATION: O6-methyl-2'-deoxyguanosine

<400> SEQUENCE: 1
tccatgacgt tcctgatgct                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (9)
<223> OTHER INFORMATION: O6-methyl-2'-deoxyguanosine

<400> SEQUENCE: 2
tccatgtcgt ccctgatgct                                                   20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (8)
<223> OTHER INFORMATION: O6-methyl-2'-deoxyguanosine

<400> SEQUENCE: 3
gctagacgtt agcgt                                                        15

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        Oligonucleotide
<220> FEATURE:
<221> NAME/KEY: modified_base
<222> LOCATION: (9)
<223> OTHER INFORMATION: O6-methyl-2'-deoxyguanosine

<400> SEQUENCE: 4
tccataacgt tcctgatgct                                            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
tccatgacgt tcctgatgct                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
<220> FEATURE:
<221> NAME/KEY: modified_base
<222> LOCATION: (8)
<223> OTHER INFORMATION: 5-methyl-2'-deoxycytidine

<400> SEQUENCE: 6
tccatgacgt tcctgatgct                                            20
```